United States Patent [19]

Rossignol

[11] Patent Number: 4,507,288

[45] Date of Patent: Mar. 26, 1985

[54] β-GLYCEROPHOSPHATE SALTS OF ANTIMALARIAL PHENANTHRENEMETHANOL COMPOUNDS

[75] Inventor: Jean F. Rossignol, Philadelphia, Pa.

[73] Assignee: Smithkline Beckman Corporation, Philadelphia, Pa.

[21] Appl. No.: 533,019

[22] Filed: Sep. 16, 1983

[51] Int. Cl.$^3$ .................... A61K 31/685; C07C 9/11
[52] U.S. Cl. ..................................... 514/143; 260/924
[58] Field of Search ......................... 260/924; 424/199

[56] References Cited

U.S. PATENT DOCUMENTS 4,178,376  12/1979  Higuchi et al. .................. 424/258
4,399,283  8/1983   Fisher et al. .................... 424/257

OTHER PUBLICATIONS

Am. J. Trop. Med. Hyg., 31(6), 1982, pp. 1075–1079.
Am. J. Trop. Med. Hyg., 25(6), 1976, pp. 769–774.
J. Med. Chem., 15(7), 1972, pp. 771–775.

Primary Examiner—Anton H. Sutto
Attorney, Agent, or Firm—Richard D. Foggio; William H. Edgerton; Alan D. Lourie

[57] ABSTRACT

The compounds of formula (I)

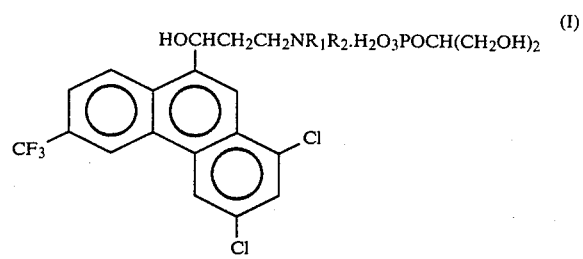

wherein $R_1$ is hydrogen or an alkyl radical containing one to six carbon atoms and $R_2$ is an alkyl radical containing one to six carbon atoms possess markedly increased activity against malaria-causing parasites. Pharmaceutical compositions and method of treatment of subjects with malaria are also disclosed.

7 Claims, No Drawings

β-GLYCEROPHOSPHATE SALTS OF ANTIMALARIAL PHENANTHRENEMETHANOL COMPOUNDS

BACKGROUND OF THE INVENTION

A number of phenanthrenemethanol compounds have been shown to exhibit antimalarial activity in humans against both chloroquine-sensitive and resistant strains of *Plasmodium falciparum*. The evaluation of the antimalarial activity of the phenanthrenemethanol, halofantrine or 1-[1,3-dichloro-6-trifluoromethyl-9-phenanthryl]-3-di-(n-butyl)-aminopropanol hydrochloride, was reported in the American Journal of Tropical Medicine and Hygiene, Vol. 31(6) pages 1075-79 (1982). Halofantrine was effective when administered over a short period of time and with a minimum of two doses against the multi-drug resistant Vietnam Smith strain and Cambodian Buchanan strain of *P. falciparum* and the Chesson strain of *P. vivax*. However, problems with systemic bioavailability remained. A means for enhancing the bioavailability of a number of phenanthrenemethanol antimalarial compounds, including halofantrine, utilizing specific organic fatty acids, as adjuvants, has been disclosed in U.S. Pat. No. 4,178,376.

SUMMARY OF THE INVENTION

This invention relates to the β-glycerophosphate salts of the class of antimalarial compounds containing halofantrine (as the free base) and its analogs. These salts exhibit markedly increased activity against malaria-causing parasites when compared to the hydrochloride salts reported in the literature. Pharmaceutical compositions and methods of treatment of subjects with malaria are also disclosed.

DETAILED DESCRIPTION OF THE INVENTION

The compounds represented by the following structural formula (I):

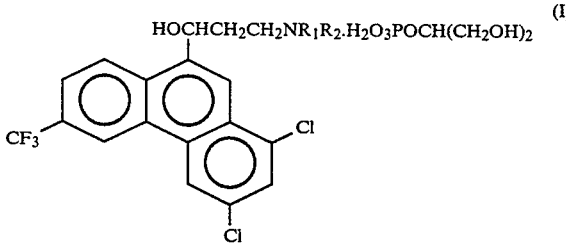

wherein $R_1$ is hydrogen or an alkyl radical containing one to six carbon atoms and $R_2$ is an alkyl radical containing one to six carbon atoms, possess markedly increased activity against malaria-causing parasites.

A particular class of compounds of this invention are those compounds of formula (I) wherein $R_1$ is an alkyl radical containing one to six carbon atoms. Exemplifying this class of compounds is 1-[1,3-dichloro-6-trifluoromethyl-9-phenanthryl]-3-di(n-butyl)amino-propanol-β-glycerophosphate, a compound of formula (I) wherein both $R_1$ and $R_2$ are n-butyl radicals.

A second class of compounds of this invention are those compounds of the formula (I) wherein $R_1$ is hydrogen. Exemplifying the class of compounds is 1-[1,3-dichloro-6-trifluoromethyl-9-phenanthryl]-3-n-butylaminopropanol-β-glycerophosphate, a compound of formula (I) wherein $R_1$ is hydrogen and $R_2$ is a n-butyl radical.

The compounds of this invention are conveniently prepared by reacting β-glycerophosphoric acid with a compound of the formula (II):

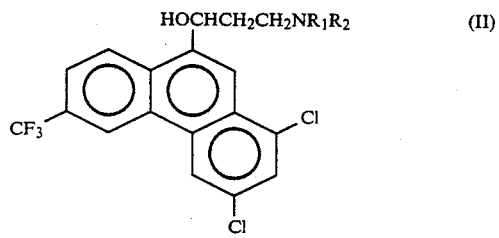

wherein $R_1$ and $R_2$ are described above in an inert solvent. The amount of glycerophosphoric acid employed in this reaction can be between 0.75 and 1.25 moles per mole of the compound of the formula (II) but equimolar amounts of both reactants are preferred. The compound of formula (II) is mixed with the appropriate amount of β-glycerophosphoric acid (50% aqueous solution) and the inert solvent is added to affect solution of the reactants at a temperature selected from the range of ambient temperature to 100° C. The reaction solution is filtered and the filtrate is heated under reduced pressure up to 100° C. to remove the solvent. Upon the removal of solvent, the compound of the formula (I) precipitates and is collected and dried.

Examples of the inert solvents which are utilized in the process are alcohols, such as, methanol, ethanol, isopropanol and the like and amides, such as dimethylformamide and dimethylacetamide.

The bases of the formula (II) are prepared according to the general procedures described in the Journal of Medicinal Chemistry, Vol. 15, No. 7, pages 771-5 (1972) wherein the process for converting substituted phenanthrene-9-carboxylic acid into the desired compounds as the free base form are detailed.

The antimalarial activities of the compounds of this invention is demonstrated in a standard pharmacological in vivo test procedure against *P. berghei* in Swiss mice.

The antimalarial activity of 1-[1,3-dichloro-6-trifluoromethyl-9-phenanthryl]-3-di(n-butyl)amino-propanol-β-glycerophosphate (Compound A) was established utilizing the following methodology. Test animals were infected by interperitoneal injection of $10^6$ parasitized cells of *P. berghei* contained in 0.5 ml of 1:400 dilution of donor mouse blood which was infected with *P. berghei* one week earlier. Three days after infection, 3 groups of 4 mice (2 males and 2 females) were treated with Compound A at a dose level of 1, 4 and 16 mg/kg/day for 4 consecutive days. Similarly, a positive control of 3 groups of 4 mice (2 males and 2 females) were treated with halofantrine, as the hydrochloride salt, at a dose level of 3, 12 and 48 mg/kg/day for 4 consecutive days. The route of administration of Compound A and halofantrine was oral intubation of a suspension of each compound in 0.2% methyl cellulose at a constant volume of 20 ml. A negative control group of 4 mice (2 males and 2 females) remained untreated. The results of the above test procedure measured in survival time in days and percent of red cells parasitized at 28 days in the treated surviving mice and at 3 days in the untreated control mice are shown below in Table I.

TABLE I

| Dose mg/k/day × 4 days | Deaths - % - Date of Death | % Red Cells Parasitized (Mean Value) |
| --- | --- | --- |
| Halofantrine (HCl) | | |
| 3 mg/kg/day | 4/4 - 100% - day 5 | — |
| 12 mg/kg/day | 2/4 - 50% - 3 | 6.5% |
| 48 mg/kg/day | 0/4 - 0% - | 3.0% |
| Compound A | | |
| 1 mg/kg/day | 4/4 - 100% - day 6 to 13 | — |
| 4 mg/kg/day | 0/4 - 0% | 0% |
| 16 mg/kg/day | 0/4 - 0% | 0% |
| Control | 4/4 - 100% - day 4 to 6 | 71.2% (day 3) |

Compound A is at least 12 times more effective, on a weight by weight basis, in the treatment of *P. berghei* malaria in mice based on survival times and clearance of parasites when compared to halofantrine hydrochloride.

The pharmaceutical compositions of this invention containing a compound of formula (I) which has antimalarial activity are prepared in conventional dosage unit forms by incorporating the chemical compound with a nontoxic pharmaceutical carrier according to accepted procedures. A nontoxic quantity of said active ingredient is chosen which is sufficient to produce the desired chemotherapeutic activity in a subject, animal or human, without unacceptable toxicity. The compositions will contain the active ingredient in such an effective but nontoxic amount selected from about 125 mg to about 1000 mg of active ingredient per dosage unit but this quantity depends on the specific biological activity desired, the activity of the compound and the conditions of the patient.

A wide variety of pharmaceutical forms can be employed. Thus, if a solid carrier for oral administration is used the preparation can be tableted, placed in a hard gelatin capsule in powder or pellet form, or in the form of a suppository, trouche or lozenge. The amount of solid carrier will vary widely but preferably will be from about 125 mg to about 500 mg. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional technique of the pharmaceutical chemist involving mixing, granulating and compressing when necessary, or variously mixing and dissolving the ingredients as appropriate to give the desired end product.

The method of producing antimalarial activity, curatively or prophylactically, comprises administering internally to a subject in need of such activity a compound of formula (I), usually combined with a pharmaceutical carrier, in a nontoxic amount sufficient to produce said activity as described above. The route of administration may be any route which effectively transports the active compound to the site of action which is to be affected within the body such as orally or parenterally. Advantageously, a single oral dose or equal oral doses will be administered several times such as from 1-3 times a day with the daily dosage regimen being selected from about 125 mg to about 1000 mg.

The following examples illustrate the preparations of the compounds of formula (I) and their incorporation into pharmaceutical compositions and as such are not to be considered as limiting the invention set forth in the claims appended hereto.

EXAMPLE 1

Preparation of 1-[1,3-dichloro-6-trifluoromethyl-9-phenanthryl]-3-di(n-butyl)aminopropanol-β-glycerophosphate (Compound A)

To a 50% aqueous solution of β-glycerophosphoric acid (4.8 g) at ambient temperature with stirring was added 1-[-1,3-dichloro-6-trifluoromethyl-9-phenanthryl]-3-di(n-butyl)aminopropanol (14.0 g). To the mixture was added ethanol (500 ml) and the mixture is heated to about 100° C. to affect solution. The solution is then filtered and the ethanol removed under vacuum until the desired product precipitates as a white crystalline material. After collecting and drying, the desired product has a melting point of 60°-65° C. Elemental analysis is as follows: Calculated C, 51.78; H, 5.80; N, 2.08 and Cl, 10.56 Found C, 51.83; H, 5.65; N, 2.10 and Cl, 10.20.

Utilizing the general procedure of Example 1 the following compounds of formula (I) are prepared from β-glycerophosphoric acid and the appropriate phenanthrenemethanol of formula (II):

| Compound | $R_1$ | $R_2$ |
| --- | --- | --- |
| B | H | n-Butyl |
| C | H | i-Propyl |
| D | H | n-Hexyl |
| E | Ethyl | Ethyl |
| F | i-Propyl | i-Propyl |
| G | n-Hexyl | n-Hexyl |

EXAMPLE 2

As a specific embodiment of a composition of this invention, an active ingredient, such as one part of Compound A, is dissolved in 20 parts of 0.2 percent aqueous methyl cellulose and is administered orally in one dose of 4 mg/kg to a subject in need of treatment of malaria.

What is claimed is:

1. A compound represented by the following structural formula (I):

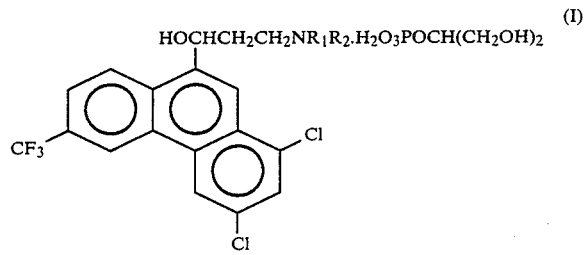

$$HOCHCH_2CH_2NR_1R_2 \cdot H_2O_3POCH(CH_2OH)_2 \qquad (I)$$

wherein $R_1$ is hydrogen or an alkyl radical containing one to six carbon atoms and $R_2$ is an alkyl radical containing one to six carbon atoms.

2. A compound of claim 1 wherein $R_1$ is an alkyl radical containing one to six carbon atoms.

3. A compound of claim 2 wherein both $R_1$ and $R_2$ are n-butyl radicals, which is 1-[1,3-dichloro-6-trifluoromethyl-9-phenanthryl]-3-di(n-butyl)aminopropanol-β-glycerophosphate.

4. A compound of claim 1 wherein $R_1$ is hydrogen.

5. A pharmaceutical composition for the treatment of malaria comprising a nontoxic antimalarial quantity of a compound of claim 1 and a pharmaceutically acceptable carrier therefor.

6. A composition of claim 5 in which the quantity of the compound is selected from the range of from 125 mg to about 1000 mg.

7. A method for the treatment of malaria in a subject in need of said treatment comprising administering orally or by injection a nontoxic antimalarial quantity of a compound of claim 1.

* * * * *